United States Patent [19]
Nicolle et al.

[11] Patent Number: 5,616,335
[45] Date of Patent: Apr. 1, 1997

[54] STABLE THICKENED DISINFECTING AQUEOUS COMPOSITION CONTAINING AN ORGANIC PEROXY ACID INTENDED FOR HUMAN OR ANIMAL USE

[75] Inventors: Remy Nicolle, Meudon; Daniel Le Rouzic, Ermont; Pascal Crisinel, Versailles; Gerard DeClerck, Saint Gratien; Henry Ledon, Versailles, all of France

[73] Assignee: Chemoxal S.A., Paris Cedex, France

[21] Appl. No.: 351,254

[22] PCT Filed: May 4, 1994

[86] PCT No.: PCT/FR94/00517

§ 371 Date: Jan. 10, 1995

§ 102(e) Date: Jan. 10, 1995

[87] PCT Pub. No.: WO94/24863

PCT Pub. Date: Nov. 10, 1994

[30] Foreign Application Priority Data

May 5, 1993 [FR] France ................... 93 05376

[51] Int. Cl.⁶ .................. A01N 25/02; A61K 47/32; A61K 31/19
[52] U.S. Cl. .................. 424/405; 514/557; 514/772.4
[58] Field of Search ................... 424/405, 78.31, 424/78.35, 78.37; 514/772.4, 557

[56] References Cited

U.S. PATENT DOCUMENTS

| | | | |
|---|---|---|---|
| 4,574,084 | 3/1986 | Berger | 424/405 |
| 4,891,216 | 1/1990 | Kross et al. | 424/661 |
| 4,900,721 | 2/1990 | Bansemir et al. | |
| 4,986,990 | 1/1991 | Davidson et al. | 424/665 |
| 5,185,161 | 2/1993 | Davidson et al. | 424/665 |
| 5,296,239 | 3/1994 | Colery et al. | |

FOREIGN PATENT DOCUMENTS

| | | |
|---|---|---|
| 0024219 | 2/1981 | European Pat. Off. |
| 0252278 | 1/1988 | European Pat. Off. |
| 0260430 | 3/1988 | European Pat. Off. |
| 0370850 | 5/1990 | European Pat. Off. |
| 0421974 | 4/1991 | European Pat. Off. |
| 0441235 | 8/1991 | European Pat. Off. |
| 2687069 | 8/1993 | France. |
| 2255507 | 11/1992 | United Kingdom. |
| WO91/14172 | 9/1991 | WIPO. |

OTHER PUBLICATIONS

H. Kuhn et al., "Versuche zur Antimikrobiellen Behandlung von Dermatologischen Zubereitungen Mittels Peressigsäure," Pharmazie, vol. 31, 1976, pp. 117–120.

H. P. Werner et al., "Destruction of Spores in Alcohol by Peracetic Acid," Chemical Abstracts, vol. 79, No. 25, 1973.

E. Fustes et al., "Teat Profylactic Disinfection Against Intramammary Infections," Chemical Abstracts, vol. 104, No. 1, 1986.

E. Fustes et al., "Teat Disinfection for the Prevention of Intramammary Infections," Chemical Abstracts, vol. 104, No. 25, 1986.

*Primary Examiner*—Carlos A. Azpuru
*Attorney, Agent, or Firm*—Oliff & Berridge

[57] ABSTRACT

The invention relates to an aqueous composition which is stable with time, containing an organic peroxy acid and at least one thickening agent in a concentration such that the viscosity of the composition is greater than 100 mPa.s, as well as the use of this composition, in particular as a disinfecting and/or cleaning agent.

48 Claims, No Drawings

STABLE THICKENED DISINFECTING AQUEOUS COMPOSITION CONTAINING AN ORGANIC PEROXY ACID INTENDED FOR HUMAN OR ANIMAL USE

The present invention relates to aqueous disinfectant compositions which are stable with time, non-irritant and have a wide antimicrobial spectrum, as well as to their uses, in particular as hygiene agents.

Numerous compositions intended for disinfection of the skin or of mucous membranes have already been marketed. Such compositions may be in liquid form and contain quarternary ammonium compounds such as chlorhexidine derivatives like chlorhexidine digluconate or compounds such as parachloromethacresol or trichlorocarbanilide as disinfecting or antiseptic agent.

These compositions usually contain various surface-active agents with a view, in particular, to favouring cleaning of the skin. They are then collectively known as "antiseptic liquid soap". However, these compositions have the main disadvantages, on the one hand, of having an antimicrobial spectrum which is limited to certain microbial populations generally chosen from Gram-positive or Gram-negative bacteria, microfungi such as yeasts or moulds, or viruses, and, on the other hand, of making possible only a small decrease in the number of a given microbial population, that is to say of having only a reduced disinfecting or antiseptic power. In order to overcome the latter disadvantage it is usually recommended to leave the disinfectant composition in contact with the skin or the mucous membrane to be disinfected for several minutes; however, even so, the decrease in the microbial population often remains insufficient. Furthermore, in common practice, it has been possible to observe that a user rarely exceeds a contact time of one minute, this contact time being more generally of the order of 30 seconds.

A need was thus expressed for disinfectant compositions having a wide antimicrobial spectrum and a strong disinfecting power which is rapidly manifested, in all cases in less than one minute and preferably in less than 30 seconds.

Moreover, it is known that organic peroxy acids have a disinfecting or antimicrobial power. Organic peroxides are usually used for the disinfection of floors and other surfaces. They are also used for the disinfection of articles which are intended to come into contact with a biological medium. Thus, aqueous solutions of peroxy acids have been described in Patent Application EP-A-472,713 as a disinfecting agent for milk vats, in Patent Application EP-A-370, 850 as a disinfecting agent for haemodialysis devices or in Patent Applications GB 2,255,507 and EP-A-421,974 as a disinfectant for large volumes which are not easily immersed and for non-horizontal surfaces. For the purpose of disinfection of such articles, the peroxy acid concentration of the disinfecting agent is always greater than 0.1% by weight, and more generally greater than 1% by weight. On account in particular of their aggressive and irritant nature, it is advisable to remove carefully, by washing with water, all trace of peroxy acids from the disinfected articles before they are placed in contact with a biological medium such as milk or blood. It is also on account of their aggressive and irritant nature for the skin and the mucous membranes that, to the knowledge of the Applicant, no disinfectant composition intended in particular for human or animal body hygiene has hitherto been marketed.

Moreover, the Applicant has been able to show that, on account of their strong oxidizing power, organic peroxy acids may degrade other additives such as surface-active agents, which it is often convenient to which are often incorporated into a composition of the antiseptic liquid soap type. Conversely, certain surfactants may sometimes rapidly degrade organic peroxy acids and cause them to lose their disinfectant properties.

The Applicant has also been able to show that these compositions containing certain additives such as surface-active agents and organic peroxy acids, while having a homogeneous appearance for a short period, may dissociate into at least two phases after a few months, or even a few weeks.

Now, compositions intended for human or animal use, which are able to be stored for several months, or even for more than a year before being used, must conserve a homogeneous appearance during such a period.

A first subject of the invention thus consists of disinfectant compositions having a wide antimicrobial spectrum as well as a strong antimicrobial power, it being possible for the latter to manifest itself after a short contact time. The compositions of the invention are, moreover, non-aggressive and non-irritant for human and animal skin and mucous membranes, and are stable with time, that is to say that they remain homogeneous and may conserve a disinfecting power even after prolonged storage, this being the case either in the presence or absence of additives such as surfactants.

Moreover, these compositions have a viscosity such that they may be used as a disinfectant or antiseptic liquid soap, or as a hygiene agent for udder teats.

A second subject of the invention consists of the use of these compositions as a hygiene agent for the disinfection of human or animal skin or mucous membranes.

The present invention consists of an aqueous composition which is stable with time, characterized in that it contains:

an organic peroxy acid in a concentration less than 0.09% by weight;

and at least one thickening agent in a concentration such that the viscosity of the composition is greater than 100 mPa.s (Brookfield LVT 2 at 20° C.).

The organic peroxy acids may more particularly be chosen from the group consisting of:

1) a monoperoxy acid of formula (I):

$$R_1-CO_3H \qquad (I)$$

in which $R_1$ represents a linear or branched $C_1-C_{24}$ alkyl radical, an aryl radical or a $C_3-C_{10}$ cycloalkyl radical, and 2) a diperoxy acid of formula (II):

$$H_3OC-R_2-CO_3H \qquad (II)$$

in which $R_2$ represents a linear or branched $C_1-C_{24}$ alkylene radical, an arylene radical or a $C_3-C_{10}$ cycloalkylene radical, each of $R_1$ and $R_2$ being substituted or otherwise with one or more functional groups or radicals.

The aryl and arylene radicals according to the invention may contain from 1 to 5 benzene rings, preferably one benzene ring, which may, where appropriate, be fused with one or more, generally 1 or 2, rings containing 5 or 7 carbon atoms.

A composition according to the invention is considered as stable with time when its peroxy acid concentration varies by less then 10% (by weight) over a period of time greater than 6 months, preferably greater than 12 months, counting from the end of the maturation time of the said composition. This maturation time is explained below.

With a view to maintaining the stability of a composition according to the invention over such a period of time, it may be entirely desirable to avoid the presence of monoalcohols such as ethanol or isopropanol. Indeed, the Applicant has been able to show that the presence of a monoalcohol induced an appreciable decrease in the stability, and thus in the peroxy acid content of the composition according to the invention.

Within the context of the present invention and except where otherwise indicated, when radicals or residues are substituted, the substituents are preferably chosen from the group consisting of the following radicals or functional groups:

a free carboxylic group in the ester or amide form, or salified by an alkali metal, alkaline-earth metal, ammonium or phosphonium counterion, a linear or branched $C_1$–$C_{24}$ alkyl radical substituted or otherwise with one or more, generally one to five, carboxylic and/or amine functions, an acyl radical of formula

R—CO—

R representing a linear or branched $C_1$–$C_{24}$ alkyl radical, a $C_1$–$C_{24}$ alkoxy radical substituted or otherwise with one or more, generally one to five, carboxylic and/or amine functions, an aryl radical, an amine, hydroxyl, nitrile, nitro, trifluoromethyl or sulphonyl function, a halogen atom such as fluorine, chlorine or bromine.

By way of preferred monoperoxy acids of formula (I) there may be mentioned those in which $R_1$ represents a $C_1$–$C_{12}$ alkyl radical. Among the organic peroxy acids of formula (I) or (II) there may in particular be mentioned the following acids:
peracetic,
perpropionic,
monoperoxyazelaic,
percaprylic,
perundecylenic,
perlauric,
monoperoxysuccinic,
monoperoxyglutaric,
diperoxysuccinic,
diperoxyazelaic,
2-octyl-1,4-peroxybutanedioic,
2-decyl-1,4-peroxybutanedioic,
2-dodecyl-1,4-peroxybutanedioic,
1,12-diperoxydodecanedioic;

peracetic acid being a particularly preferred organic peroxide in the context of the present invention.

Peroxybenzoic acid and its derivatives such as metachloroperoxybenzoic, p-tert-butylperoxybenzoic, p-nitroperoxybenzoic, monoperphthalic or aminophthaloylperacetic acids may also be advantageously used.

By way of monoperoxy acid of formula (I) there may also be mentioned the imidoperoxy acids of formula (III):

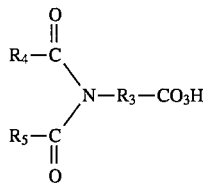

(III)

in which $R_3$ is a radical having one of the meanings of $R_2$, $R_3$ being substituted or otherwise with one or more functional groups or radicals and $R_4$ and $R_5$ are identical or different and represent a linear or branched $C_1$–$C_8$ alkyl radical substituted or otherwise with one or more functional groups or radicals, or $R_4$ and $R_5$ together form a linear, saturated or mono-unsaturated $C_2$–$C_4$ aliphatic residue, substituted or otherwise with a linear or branched $C_1$–$C_{24}$ alkyl radical.

Among the compounds of formula (III), those are preferred which include a nitrogen-containing heterocycle, of formula (IV):

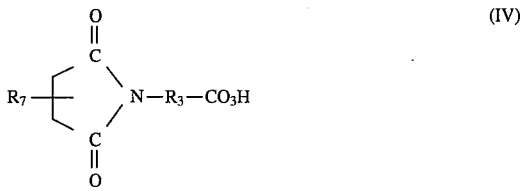

in which $R_3$ is a residue as indicated above and $R_7$ is a linear or branched $C_1$–$C_{24}$ alkyl radical, substituted or otherwise with one or more functional groups or radicals, or $R_7$ is an aryl group fused with the nitrogen-containing heterocycle, substituted or otherwise with one or more functional groups or radicals.

$R_3$ is advantageously a $C_1$–$C_{20}$, preferably a $C_1$–$C_{14}$, alkylene radical; and $R_7$ is a phenylene radical fused with the nitrogen-containing heterocycle.

By way of example of such compounds there may be mentioned phthalimidoperacetic acid, phthalimidoperpropionic acid, phthalimidoperdodecanoic acid or phthalimidopercaproic acid.

The organic peroxy acids which may be used in the composition according to the invention may be prepared in a known manner, for example according to the processes described in European Patent Application Nos. 24,219 and 441,235.

The concentration of organic peroxy acid in the composition may be between 0.001% and 0.05% by weight and preferably between 0.002% and 0.025% by weight.

Preferred viscosity modifying agents may be chosen from polyoxyethylated (POE) compounds, polyoxypropylated (POP) compounds or polyoxyethylated and polyoxypropylated (POE-POP) compounds.

Such compounds may be chosen from those corresponding to the formula (V):

$$R_8\text{—O(Z)H} \qquad (V)$$

in which $R_8$ is H, a saturated or unsaturated linear or branched $C_1$–$C_{30}$, preferably $C_{10}$–$C_{24}$, aliphatic radical or an aryl radical, it being possible for $R_8$, when it is other than H, to be substituted or otherwise with one or more functional groups or radicals,
and Z is a POE or POP polymer residue consisting, respectively, of ($CH_2CH_2O$) or

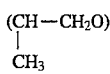

moieties, or a POE-POP copolymer residue consisting of ($CH_2CH_2O$) and

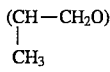

moieties
these moieties being distributed in a systematic or random (statistical) manner.

The residue Z may represent a copolymer residue containing at least one polyoxyethylene unit POE and at least one, and preferably two, polyoxypropylene units POP. Moreover, $R_8$ may advantageously represent hydrogen.

Such compounds may, for example, be those represented by the formulae:

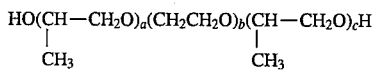

or

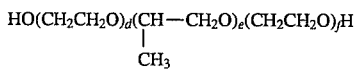

where a, b, c, d, e and f represent the number of EO and PO moieties of the POE and POP units. These compounds are in particular marketed by BASF-Wyandette Corp. under the tradename Pluronic®.

Other POE, POP or POE-POP compounds which may be used as viscosity modifying agents according to the invention, are described in C.T.F.A. International Cosmetic Ingredients Dictionary, 4th Edition 1991, in particular pp. 376–428 and 474–505.

However, preferred viscosity modifying agents in the context of the present invention are polyether-urethanes.

These compounds are described in the Patent Application FR-A-2,687,069, in the name of L'OREAL, in particular page 2, line 19 to page 3, line 25, as well as in Patent Application EP-A-260,430 in the name of AKZO. These patent applications are included here for reference.

The polyether-urethanes which may be used according to the invention correspond to the following formula (VI):

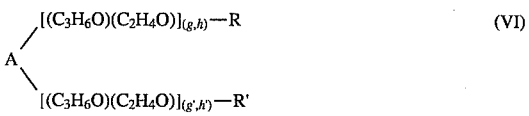

where: $[(C_3H_6O)(C_2H_4O)](g_i, h_i)$
with $(g_i, h_i)$ denoting (g, h) or (g', h'), means that it is a statistical polymer of propylene oxide and ethylene oxide containing h moles of ethylene oxide and g moles of propylene oxide, distributed randomly within the polymer chain;

A denotes an aliphatic, cycloaliphatic or aromatic diisocyanate residue, preferably a polymethylene diisocyanate, toluylene diisocyanate or methanediphenyl diisocyanate residue;

R and R', which may be identical or different, denote a $C_8$–$C_{30}$, preferably a $C_{10}$–$C_{20}$ and more particularly a $C_{12}$–$C_{18}$, alkenyl or alkyl radical; $g_i$ and $h_i$, which may be identical or different, being such that the sum of $g_i + h_i$ varies from 20 to 200 moles and preferably from 60 to 120 moles; the $h_i/g_i$ molar ratio is between 30/90 and 90/10 and more particularly between 70/30 and 85/15.

The more particularly preferred compounds of formula (VI) are those in which A denotes the hexamethylene diisocyanate residue and R and R' denote a lauryl radical or a mixture of radicals derived from tallow.

The radicals $R_i$–$[(C_2H_4O)-(C_3H_6O)](g_i, h_i)$ preferably have a molecular weight of the order of 4,000, with $R_i$ denoting R or R' and $g_i$ and $h_i$ denote g or h or g' and h', as defined above.

The compounds of formula (VI) may be obtained by reacting a diisocyanate with one or two polyoxyethylenated and polyoxypropylenated fatty alcohols, of formula $R_i[(OC_2H_4)-(OC_3H_6)]OH(g_i, h_i)$, in which $R_i$, $g_i$ and $h_i$ have the meanings indicated above, which is(are) used in excess relative to the diisocyanate, in order to totally consume the latter.

Very particularly preferred viscosity modifying agents of formula (VI) are those marketed by the company AKZO under the name DAPRAL, such as DAPRAL T210, DAPRAL T212 or DAPRAL GT282.

The average molecular weight of the compounds of formula (V) and of formula (VI) may be between 1,000 and 20,000, preferably between 3,000 and 10,000.

Finally, by way of other viscosity modifying agents which may be used, there may be mentioned the compounds referred to in C.T.F.A. International Cosmetic Ingredients Dictionary, under the name Ceteareth such as Ceteareth-33 marketed by the company Seppic under the name CTO Lanol Wax.

The concentration of viscosity modifying agent in the composition is preferably such that the viscosity of the said composition is advantageously between 100 and 700 mPa.s, more preferably between 150 and 700 mPa.s. The viscosity values are measured using a Brookfield LVT2 viscosimeter at 20° C.

The compositions according to the invention may additionally contain one or more surfactants chosen from amphoteric and cationic surfactants or preferably nonionic and anionic surfactants.

These surfactants may impart a cleaning, foaming or wetting effect to the composition according to the invention. They are more generally used in formulations of the disinfectant liquid soap type or in compositions intended for udder teat hygiene.

Surprisingly, the presence of these surfactants does not result in a decrease in the stability with time of the composition according to the invention.

The composition thus remains active and has a homogeneous appearance, even when it is stored for several months, or even for several years.

By way of anionic surfactants, there may be mentioned alkyl ether sulphates, alkylbenzene sulphonates, alkyl sulphates, olefin sulphonates and alkyl ether carboxylates, salified with one or more counterions, such as an alkali metal ion like sodium or potassium, or an alkaline-earth metal ion. A preferred anionic surfactant is sodium lauryl ether sulphate.

By way of nonionic surfactant, there may be mentioned fatty acid esters of sorbitan, polyoxyethylated (POE) and/or polyoxypropylated (POP) fatty acid esters of sorbitan and preferably alkylpolyglycosides of formula (VII)

where G is a reducing sugar residue containing 5 or 6 carbon atoms, x is a number between 1 and 10, $R_9$ is a saturated or unsaturated linear or branched $C_6$–$C_{24}$ aliphatic radical, $R_{10}$ is an alkylene group having from 2 to 4 carbon atoms and z is between 0 and 20.

G may more particularly be a glucose residue when x is between 1 and 5, $R_9$ is an alkyl radical containing from 8 to 18 carbon atoms and z is equal to zero.

The surfactant concentration in the composition may be between 0.1 and 15% by weight, preferably between 1 and 7% by weight.

The compositions according to the invention may additionally include other additives, such as emollients, colouring agents, softening agents and sequestrating agents.

Moreover, since organic peroxy acids are conventionally obtained by reacting an organic acid with hydrogen peroxide, the compositions according to the invention may also include such compounds. The hydrogen peroxide concentration in the composition is usually less than 8% by weight, preferably between 0.1% and 3% by weight, the organic acid concentration in the composition is generally less than 1.5% by weight, preferably between 0.1 and 1% by weight. Stabilizing agents for the organic peroxy acids, such as sodium hydrogen pyrophosphate, may also be contained in the composition.

The compositions according to the invention may be prepared by mixing, with stirring, an aqueous solution of an organic peroxy acid which is ready for use with the thickening agent and water as well as, where appropriate, the surfactant(s) and the other additives mentioned above.

Alternatively, the compositions of the invention may be prepared by mixing, with stirring, hydrogen peroxide, an organic acid which is a precursor of a chosen organic peroxy acid and the other constituents of the composition.

The contents of hydrogen peroxide and of organic acid are chosen such that after a certain maturation time, the desired organic peroxy acid concentration is obtained. This maturation time may be between 15 days and six months.

This maturation time may be considerably reduced when the mixtures obtained as indicated above are subjected to a temperature between 30° and 45° C., preferably between 35° and 43° C. In this way, the maturation time may be less than 3 days.

The compositions according to the invention described above may be used as hygiene agents for the disinfection of human or animal skin or mucous membranes.

They may in particular be used as disinfecting and/or cleaning agent, in particular as hygiene agents for the disinfection of udder teats. For this use, it is possible for the compositions to contain only low contents of peroxy acids, for example contents between 0.001% and 0.005% by weight.

The compositions according to the invention may also be used as cleaning and antiseptic or antimicrobial soaps, in particular in liquid form. In this use, the compositions most often include at least one surface-active agent as defined above.

Since the compositions according to the invention are viscous, they are of great value in this type of use, insofar as they remain in intimate contact with the skin or the mucous membrane to be disinfected for the required time lapse, after which they may be removed simply by washing with water.

It is important to note that the viscosity of these compositions remains stable for several months, or even for several years.

The aim of the examples which follow is to illustrate the present invention.

In these examples, the percentages are by weight and the viscosities are measured using a Brookfield LVT2 viscosimeter at 40 revolutions/minute at 20° C.

EXAMPLE 1

Liquid Disinfectant Soap 500 g of distilled water are introduced into a mechanically stirred two-liter reactor, followed by:

0.2 g of sodium hydrogen pyrophosphate, 40 g of Dapral T 210[1]

[1]: viscosity modifying agent marketed by the company Akzo.

20 g of sodium lauryl ether sulphate 39 g of 70% hydrogen peroxide 4.2 g of acetic acid, 20 g of decylglucoside, 3.2 g of a peracetic acid solution at a concentration of 10% by weight, qs for 1,000 g of distilled water.

After an equilibrating period of 1 month at room temperature, the peracetic acid content of the composition reaches 0.01%, the hydrogen peroxide content is 2.8% and the viscosity of the solution is 430 mPa.s.

EXAMPLE 2

Liquid Disinfectant Soap 500 g of distilled water are introduced into a mechanically stirred two-liter reactor:

0.2 g of sodium hydrogen pyrophosphate, 40 g of Dapral T 210[1]

[1]: viscosity modifying agent marketed by the company Akzo.

20 g of sodium lauryl ether sulphate 39 g of 70% hydrogen peroxide 4.2 g of acetic acid, 10 g of capryl-caprylylglucoside (capryl/caprylyl molar ratio=50/50)

3.2 g of a peracetic acid solution at a concentration of 10%, qs for 1,000 g of distilled water.

After an equilibrating period of 1 month at room temperature, the peracetic acid content reaches 0.01%, the hydrogen peroxide content is 2.8% and the viscosity of the solution is 280 mPa.s.

The liquid disinfectant soaps of Examples 1 and 2 were tested on 3 rabbits. They proved to be non-irritant for the skin and very mildly irritant for the eye.

Evaluation of the ocular tolerance was carried out according to the official method, defined by the decree of 3 May 1990, published in the Journal Officiel de la République Française of 14 Nov. 1990.

Evaluation of the skin tolerance was carried out according to the official method, defined by the decree of 1 Feb. 1982, published in the Journal Officiel de la République Française of 21 Feb. 1982.

EXAMPLE 3

Liquid Disinfectant Soap

Into a mechanically stirred two-liter reactor were first of all introduced 500 g of a solution containing:

0.04% of peracetic acid,

1% of acetic acid, 5.6% of hydrogen peroxide, 0.04% of sodium pyrophosphate, qs for 500 g of distilled water, followed by:

40 g of Dapral T 210[1]

[1]: viscosity modifying agent marketed by the company Akzo.

40 g of sodium lauryl ether sulphate, qs for 1,000 g of distilled water.

After an equilibrating period of 5 months at room temperature, the peracetic acid content reaches 0.01% and the hydrogen peroxide content is 2.8%. This composition is stable for more than 18 months.

EXAMPLE 4

Liquid Disinfectant Soap

The procedure is as in Example 3, but with replacement of the 40 g of sodium lauryl ether sulphate by 20 g of this same surfactant and 10 g of capryl-caprylylglucoside (capryl/caprylyl molar ratio=50/50).

At equilibrium, the peracetic acid content is 0.01% and that of hydrogen peroxide is 2.8%.

This composition is stable for more than 18 months.

The bactericidal power of the liquid soaps of Examples 3 and 4 was tested according to the protocol NFT 72-151 under the following conditions:

test temperature: 32° C.

bacteria tested: *Staphylococcus aureus* CNCM 53514 contact time: 1 min.

dilution: pure and diluted to ½ method involving filtration on a 0.45 μm membrane.

Both the liquid soaps made it possible to decrease the initial population of the bacteria tested by a factor of $10^7$.

EXAMPLE 5

Disinfectant Composition for Udder Teat Hygiene

Approximately 500 g of distilled water are introduced into a mechanically stirred 2-liter reactor, followed by:

0.2 g of sodium hydrogen pyrophosphate, 0.5 g of allantoin, 100 g of 98% glycerol 35 g of Dapral T 210[1]

[1]: Viscosity modifying agent marketed by the company Akzo.

5.6 g of sodium lauryl ether sulphate, 10 g of decylglucoside 13.7 g of 70% hydrogen peroxide, 3.1 g of acetic acid, 2.7 g of a 10% peracetic acid solution, qs for 1,000 g of distilled water.

At equilibrium, the peracetic acid content reaches 0.0030% and the hydrogen peroxide content is 1.0%.

The viscosity of the solution is 160 mPa.s.

These two constituents are stable in this formulation for more than a year.

The bactericidal power of this composition was tested according to the protocol NFT 72-150 under the following conditions:

test temperature: room temperature bacteria tested:
  1) *Staphylococcus aureus* CNCM 53154, and
  2) *Escherichia coli* CNCM 54127 contact time: 5 minutes dilution: ½ and ¼ diluent: hard water test method: dilution-neutralization.

This composition made it possible to reduce the initial population of the bacteria tested by a factor of at least $10^5$, equally well for the *Staphylococcus aureus* and *Escherichia coli* bacteria.

The fungicidal power of this composition was tested under the following conditions:

fungus tested: *Candida albicans* CNCM 11.80 test temperature: room temperature contact time: 15 minutes diluent: hard water dilution: pure and diluted to ½ method: filtration on a 0.45 μm membrane.

This composition made it possible to reduce the population of fungus tested by a factor of at least $10^4$.

We claim:

1. Aqueous composition which is stable with time, wherein said composition comprises:

water;

an organic peroxy acid in a concentration less than 0.09% by weight; and at least one thickening agent having the formula:

$$A \begin{matrix} \diagup [(C_3H_6O)(C_2H_4O)]_{(g,h)} - R \\ \diagdown [(C_3H_6O)(C_2H_4O)]_{(g',h')} - R' \end{matrix}$$

in which: $[(C_3H_6O)(C_2H_4O)]_{(gi,hi)}$ with $(g_i,h_i)$ denoting (g,h) or (g',h'), represents a statistical polymer of propylene oxide and ethylene oxide containing $h_i$ moles of ethylene oxide and $g_i$ moles of propylene oxide, distributed randomly within the polymer chain;

A denotes an aliphatic, cycloaliphatic or aromatic diisocyanate residue;

R and R', which may be identical or different, denote a $C_8$–$C_{30}$ alkyl or alkenyl radical;

$g_i$ and $h_i$, which are identical or different, are such that $g_i+h_i$ is a number between 20 and 200;

the $h_i/g_i$ molar ratio is between 30/70 and 90/10, said thickening agent being in a concentration such that the viscosity of the composition is greater than 100 mPa.s as measured using Brookfield LVT at 20° C.

2. Aqueous composition which is stable with time, comprising:

an organic peroxy acid in a concentration less than 0.09% by weight; and at least one thickening agent having the formula:

$$A \begin{matrix} \diagup [(C_3H_6O)(C_2H_4O)]_{(g,h)} - R \\ \diagdown [(C_3H_6O)(C_2H_4O)]_{(g',h')} - R' \end{matrix}$$

in which: $[(C_3H_6O)(C_2H_4O)]_{(gi,hi)}$ with $(g_i,h_i)$ denoting (g,h) or (g',h'), represents a statistical polymer of propylene oxide and ethylene oxide containing $h_i$ moles of ethylene oxide and $g_i$ moles of propylene oxide, distributed randomly within the polymer chain;

A denotes an aliphatic, cycloaliphatic or aromatic diisocyanate residue;

R and R', which may be identical or different, denote a $C_8$–$C_{30}$ alkyl or alkenyl radical;

$g_i$ and $h_i$, which are identical or different, are such that $g_i+h_i$ is a number between 20 and 200;

the $h_i/g_i$ molar ratio is between 30/70 and 90/10, said thickening agent being in a concentration such that the viscosity of the composition is greater than 100 mPa.s as measured using Brookfield LVT 2 at 20° C., wherein said composition is substantially free of monohydric alcohol.

3. Composition according to claim 2, wherein the organic peroxy acid is selected from the group consisting of:

1) a monoperoxy acid of formula (I):

$$R_1-CO_3H \qquad (I)$$

in which $R_1$ represents a saturated or unsaturated linear or branched $C_1-C_{24}$ aliphatic radical, an aryl radical or a $C_3-C_{10}$ cycloalkyl radical, 2) a diperoxy acid of formula (II):

$$H_3OC-R_2-CO_3H \qquad (II)$$

in which $R_2$ represents a saturated or unsaturated linear or branched $C_1-C_{24}$ aliphatic radical, an arylene radical or a $C_3-C_{10}$ cycloalkylene radical, each of $R_1$ and $R_2$ being substituted or otherwise with one or more functional groups or radicals.

4. Composition according to claim 3, wherein the organic peroxy acid is a compound of the formula $R_iCO_3H$, where $R_i$ is a $C_1-C_{12}$ alkyl radical.

5. Composition according to claim 3, wherein the organic peroxy acid is peracetic acid.

6. Composition according to claim 2, wherein the organic peroxy acid is an imidoperoxy acid of formula (III):

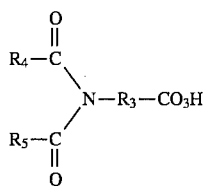

(III)

in which $R_3$ represents a saturated or unsaturated linear or branched $C_1-C_{24}$ aliphatic radical, an arylene radical or a $C_3-C_{10}$ cycloalkyl radical, $R_3$ is optionally substituted with one or more functional groups or radicals and $R_4$ and $R_5$ are identical or different and represent a linear or branched $C_1-C_8$ alkyl radical, optionally substituted with one or more functional groups or radicals, or $R_4$ and $R_5$ together form a linear, saturated or mono-unsaturated $C_2-C_4$ aliphatic residue, optionally substituted with a linear or branched $C_1-C_{24}$ alkyl radical.

7. Composition according to claim 6, wherein the organic peroxy acid is an imidoperoxy acid including a nitrogen-containing heterocycle, of formula (IV)

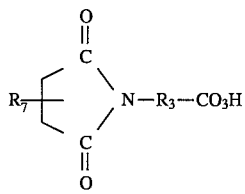

(IV)

in which $R_3$ represents a saturated or unsaturated linear or branched $C_1-C_{24}$ aliphatic radical, an arylene radical or a $C_3-C_{10}$ cycloalkylene radical, and $R_7$ is a linear or branched $C_1-C_{24}$ alkyl radical, optionally substituted with one or more functional groups or radicals, or $R_7$ is an aryl group fused with the nitrogen-containing heterocycle, optionally substituted with one or more functional groups or radicals.

8. Composition according to claim 7, wherein in the formula (IV), $R_3$ is a $C_1-C_{20}$ alkylene radical and $R_7$ is a phenylene radical fused with the nitrogen-containing heterocycle.

9. Composition according to claim 2 wherein the organic peroxy acid concentration is between 0.001% and 0.05% by weight.

10. Composition according to claim 2 wherein A denotes a polymethylene diisocyanate, toluylene diisocyanate or methanediphenylene diisocyanate residue.

11. Composition according to claim 2 wherein A denotes the hexamethylene diisocyanate residue and R and R' denote a lauryl radical or a mixture of radicals derived from tallow.

12. Composition according to claim 2, wherein the viscosity of the composition is between 100 and 700 mPa.s as measured using Brookfield LVT 2 at 20° C.

13. Composition according to claim 2 further comprising at least one anionic surfactant, salified with one or more cations.

14. Composition according to claim 13, wherein the anionic surfactant is sodium lauryl ether sulphate.

15. Composition according to claim 2 further comprising at least one nonionic surfactant.

16. Composition according to claim 2, wherein the organic peroxy acid concentration is between 0.002% and 0.025% by weight.

17. Composition according to claim 2, wherein
at least one of R and R' denotes a $C_{10}-C_{20}$ alkyl or alkenyl radical;

$g_i+h_i$ is a number between 60 and 120; and the $h_i/g_i$ molar ratio is between 50/50 and 90/10.

18. Composition according to claim 2, wherein the molecular weight of the compound of formula (VI) is between 1,000 and 20,000.

19. Composition according to claim 18, wherein said molecular weight is between 3,000 and 10,000.

20. Composition according to claim 12, wherein said viscosity of the composition is between 150 and 700 mPa.s.

21. Composition according to claim 13, wherein the at least one anionic surfactant is selected from the group consisting of alkyl ether sulphates, alkylbenzene sulphonates, alkyl sulphates, olefin sulphonates and alkyl ether carboxylates.

22. Composition according to claim 15, wherein the at least one nonionic surfactant is selected from the group consisting of fatty acid esters of sorbitan, optionally polyoxyethylated or polyoxypropylated or both, and alkylpolyglycosides of formula (VII):

$$R_9O(R_{10}O)_z(G)_x \qquad (VII)$$

where G is a reducing sugar residue containing 5 or 6 carbon atoms, x is a number between 1 and 10, $R_9$ is a saturated or unsaturated linear or branched $C_6-C_{24}$ aliphatic radical, $R_{10}$ is an alkylene group having from 2 to 4 carbon atoms and z is between 0 and 20.

23. A method for disinfecting human or animal skin or mucous membranes, comprising applying a composition according to claim 2 to human or animal skin or mucous membranes.

24. A method for disinfecting an udder teat, comprising applying a composition according to claim 2 to an udder teat.

25. Composition according to claim 22 wherein in the formula (VII):

G is a glucose or fructose residue, x is between 1 and 5, $R_9$ is an alkyl radical containing from 8 to 18 carbon atoms and z is equal to 0.

26. Composition according to claim 1, wherein the organic peroxy acid is selected from the group consisting of:

(1) a monoperoxy acid of formula (I):

$$R_1-CO_3H \qquad (I)$$

in which $R_1$ represents a saturated or unsaturated linear or branched $C_1-C_{24}$ aliphatic radical, an aryl radical or a $C_3$–$C_{10}$ cycloalkyl radical, and (2) a diperoxy acid of formula (II):

$$H_3OC-R_2-CO_3H \quad (II)$$

in which $R_2$ represents a saturated or unsaturated linear or branched $C_1$–$C_{24}$ aliphatic radical, an arylene radical or a $C_3$–$C_{10}$ cycloalkylene radical, each of $R_1$ and $R_2$ being substituted or otherwise with one or more functional groups or radicals.

27. Composition according to claim 26, wherein the organic peroxy acid is a compound of formula (I), where $R_1$ is a $C_1$–$C_{12}$ alkyl radical.

28. Composition according to claim 26, wherein the organic peroxy acid is peracetic acid.

29. Composition according to claim 1, wherein the organic peroxy acid is an imidoperoxy acid of formula (III):

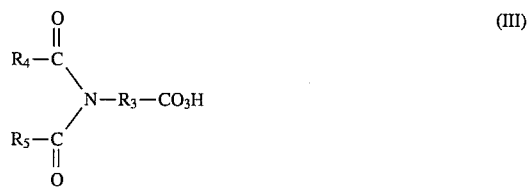

in which $R_3$ represents a saturated or unsaturated linear or branched $C_1$–$C_{24}$ aliphatic radical, an arylene radical or a $C_3$–$C_{10}$ cycloalkyl radical, $R_3$ is optionally substituted with one or more functional groups or radicals and $R_4$ and $R_5$ are identical or different and represent a linear or branched $C_1$–$C_8$ alkyl radical, optionally substituted with one or more functional groups or radicals, or $R_4$ and $R_5$ together form a linear, saturated or mono-unsaturated $C_2$–$C_4$ aliphatic residue, optionally substituted with a linear or branched $C_1$–$C_{24}$ alkyl radical.

30. Composition according to claim 29, wherein the organic peroxy acid is an imidoperoxy acid including a nitrogen-containing heterocycle, of formula (IV)

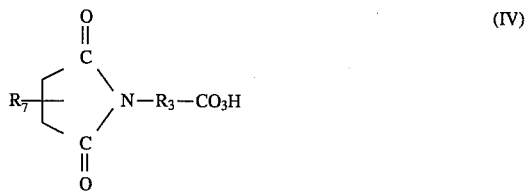

in which $R_3$ represents a saturated or unsaturated linear or branched $C_1$–$C_{24}$ aliphatic radical, an arylene radical or a $C_3$–$C_{10}$ cycloalkylene radical, and $R_7$ is a linear or branched $C_1$–$C_{24}$ alkyl radical, optionally substituted with one or more functional groups or radicals, or $R_7$ is an aryl group fused with the nitrogen-containing heterocycle, optionally substituted with one or more functional groups or radicals.

31. Composition according to claim 30, wherein in the formula (IV), $R_3$ is a $C_1$–$C_{20}$ alkylene radical and $R_7$ is a phenylene radical fused with nitrogen-containing heterocycle.

32. Composition according to claim 1, wherein the organic peroxy acid concentration is between 0.001% and 0.05% by weight.

33. Composition according to claim 1, wherein the organic peroxy acid concentration is between 0.002% and 0.025% by weight.

34. Composition according to claim 1, wherein A denotes a polymethylene diisocyanate, toluylene diisocyanate or methanediphenylene diisocyanate residue.

35. Composition according to claim 1, wherein A denotes the hexamethylene diisocyanate residue and wherein R and R' denote a lauryl radical or a mixture of radicals derived from tallow.

36. Composition according to claim 1, wherein the viscosity of the composition is between 100 and 700 mPa.s as measured using Brookfield LVT 2 at 20° C.

37. Composition according to claim 1, further comprising at least one anionic surfactant salified with one or more cations.

38. Composition according to claim 37, wherein the anionic surfactant is sodium lauryl ether sulphate.

39. Composition according to claim 1, further comprising at least one nonionic surfactant.

40. Composition according to claim 1, wherein at least one of R and R' denotes a $C_{10}$–$C_{20}$ alkyl or alkenyl radical;

$g_i + h_i$ is a number between 60 and 120; and the $h_i/g_i$ molar ratio is between 50/50 and 90/10.

41. Composition according to claim 1, wherein the molecular weight of the compound of formula (VI) is between 1,000 and 20,000.

42. Composition according to claim 41, wherein said molecular weight is between 3,000 and 10,000.

43. Composition according to claim 36, wherein said viscosity of the composition is between 150 and 700 mPa.s.

44. Composition according to claim 37, wherein the at least one anionic surfactant is selected from the group consisting of alkyl ether sulphates, alkylbenzene sulphonates, alkyl sulphates, olefin sulphonates and alkyl ether carboxylates.

45. Composition according to claim 39, wherein the at least one nonionic surfactant is selected from the group consisting of fatty acid esters of sorbitan, optionally polyoxyethylated or polyoxypropylated or both, and alkylpolyglycosides of formula (VII):

$$R_9O(R_{10}O)_z(G)_x \quad (VII)$$

where G is a reducing sugar residue containing 5 or 6 carbon atoms, x is a number between 1 and 10, $R_9$ is a saturated or unsaturated linear or branched $C_6$–$C_{24}$ aliphatic radical, $R_{10}$ is an alkylene group having from 2 to 4 carbon atoms and z is between 0 and 20.

46. Composition according to claim 44, wherein in the formula (VII):

G is a glucose or fructose residue,

X is between 1 and 5, $R_9$ is an alkyl radical containing from 8 to 18 carbon atoms, and z is equal to 0.

47. A method for disinfecting human or animal skin or mucous membranes comprising applying a composition according to claim 1 to human or animal skin or mucous membranes.

48. A method for disinfecting an udder teat, comprising applying a composition according to claim 1 to an udder teat.

* * * * *